US007951582B2

(12) United States Patent
Gazit et al.

(10) Patent No.: US 7,951,582 B2
(45) Date of Patent: May 31, 2011

(54) SYSTEMS AND METHODS FOR ANALYZING AND MANIPULATING BIOLOGICAL SAMPLES

(75) Inventors: Dan Gazit, Maccabim (IL); Boris Rubinsky, Givataim (IL); Gadi Pelled, Rishon-LeZion (IL); Zulma Gazit, Maccabim (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 194 days.

(21) Appl. No.: 12/086,780

(22) PCT Filed: Nov. 6, 2006

(86) PCT No.: PCT/IL2006/001279
§ 371 (c)(1),
(2), (4) Date: Jun. 19, 2008

(87) PCT Pub. No.: WO2007/072472
PCT Pub. Date: Jun. 28, 2007

(65) Prior Publication Data
US 2009/0029407 A1 Jan. 29, 2009

Related U.S. Application Data

(60) Provisional application No. 60/751,296, filed on Dec. 19, 2005.

(51) Int. Cl.
*C12M 3/00* (2006.01)
*C12Q 1/02* (2006.01)
(52) U.S. Cl. ............... 435/287.1; 435/285.2; 435/29

(58) Field of Classification Search .............. None
See application file for complete search history.

(56) References Cited

U.S. PATENT DOCUMENTS

| | | | | |
|---|---|---|---|---|
| 4,219,411 A | * | 8/1980 | Yen et al. | 209/213 |
| 5,837,200 A | | 11/1998 | Diessel et al. | |
| 6,200,532 B1 | * | 3/2001 | Wu et al. | 422/73 |
| 2004/0014201 A1 | | 1/2004 | Kim et al. | |

FOREIGN PATENT DOCUMENTS

DE 10137665 11/2002

OTHER PUBLICATIONS

Lin et al. Electroporation Microchips for Continuous Gene Transfection; Sensors and Acuators B, vol. 79 (2001) pp. 137-143.*
Benjamin, R. Metal Detecting-Understanding the Technology is Important. Nov. 15, 2005 published online at http//www.buzzle.com/editorials/Nov. 15, 2005-81434.asp.*
International Search Report and the Written Opinion Dated May 30, 2007 From the International Searching Authority Re.: Application No. PCT/IL2006/001279.
Communication Relating to the Results of the Partial International Search Dated Mar. 14, 2007 From the International Searching Authority Re.: Application No. PCT/IL2006/001279.

* cited by examiner

*Primary Examiner* — Jon P Weber
*Assistant Examiner* — Paul C. Martin

(57) ABSTRACT

A system for qualifying cells of a cell sample labeled with a magnetic or magnetizable moiety is provided. The system includes a cell sample holder for holding a cell of the cells and a first cell analyzer which includes a magnetic field source for applying a magnetic field to the cell and a sensor for qualifying and/or quantifying an effect of the magnetic field on the cell.

34 Claims, 5 Drawing Sheets
(4 of 5 Drawing Sheet(s) Filed in Color)

SYSTEMS AND METHODS FOR ANALYZING AND MANIPULATING BIOLOGICAL SAMPLES

RELATED APPLICATIONS

This Application is a National Phase of PCT Patent Application No. PCT/IL2006/001279 having International filing date of Nov. 6, 2006, which claims the benefit of U.S. Provisional Patent Application No. 60/751,296 filed on Dec. 19, 2005. The contents of the above Applications are all incorporated herein by reference.

FIELD AND BACKGROUND OF THE INVENTION

The present invention relates to systems and methods for analyzing samples, in particular cell samples and, more particularly, to a cell sorting system which enables accurate and rapid sorting of individual cells based on magnetic properties of cell specific tags as well as other characterizing properties and in addition enables efficient cell manipulation (e.g. genetic engineering) followed by optional cryo preservation at A single cell level.

Numerous approaches for screening samples for the presence of specific cell types or analytes are known in the art. For example, fluorescence activated cell sorting (FACS) is a technique often used to identify and isolate cells of interest based on the presence of a cell specific optical marker. Magnetic activated cell sorting (MACS) is also known in the literature and is based on the presence of a cell specific magnetic marker.

Isolation of specific cell types from cell samples (e.g. biological samples or cell cultures) is important in both diagnostic and therapeutic medicine.

For example, identification of specific cell types in a cell sample derived from a subject can indicate the presence of a pathology (e.g. cancer) or predisposition to such a pathology while isolation of adult stem cells (e.g. mesenchymal stem cells—MSCs) can be used in subsequent cell therapy.

The latter use is of particular importance since strategies for regenerating tissue are being developed in response to a range of clinical needs, including replacement of damaged or genetically absent metabolic functions and repair or restructuring of damaged tissues.

Due to limitations associated with isolation and use of embryonic stem cells, MSCs and hematopoietic stem cells (HSCs) are increasingly gaining favor as potential sources for cell therapy. Such cells can be used to generate neural, skeletal as well as hematopoietic progenitors and as such can be used in a variety of cell based therapies.

Isolation of specific cell types is typically effected through unique cellular markers or characterizing traits. Separation procedures, such as FACS, typically utilize tags (e.g. fluorescent antibodies) that specifically bind the cell of interest. Such tags can be directed at cell surface markers (e.g., CD4 and CD8 on lymphocytes) or at cytoplasmic or nuclear markers (specific gene sequence).

The key steps in the process of separation is the ability to identify and label a particular marker/characteristic of interest on a cell using a cell specific tag and use a property of the tag to manipulate the cell. Numerous types of tags exist in the art including fluorescently labeled antibodies, antibodies linked to a member of a binding pair (e.g. avidin-biotin), receptor-specific ligands labeled with fluorescent dyes and the like. For a review of commonly used cell tags, please see, Introduction to Flow Cytometry, Cambridge University Press, James V. Watson, Apr. 26, 1991).

One approach for cell manipulation involves use of tags, which include magnetic, conductive or paramagnetic particles. Such tags can be manipulated by a magnetic field and thus cells attached thereto can be isolated using the magnetic property of the tag. A review of magnetic cell tagging approaches is provided by Chalmers et al in "Flow Through, Immunomagnetic Cell Separation Biotechnol" (Prog. 1998, 14, 141-148; and DePalma in "Developments in Biomagnetic Separations Focus on New Affinity Mechanisms" (Genet. Eng. News 1997, 17, 11).

Although systems capable of magnetic separation of tagged cells are known in the art such systems are incapable of typing non-tagged cells and thus are limited to bulk sorting and isolation of desired cells only. In addition, prior art systems are also limited by a lack of cell manipulation and preservation capabilities, and thus cells sorted by such systems must be further processed to enable preservation, a severe limitation especially in cases were the cells of interest must be manipulated as part of the process and stored under cell preserving conditions.

Thus, it would be highly advantageous to have a system devoid of the above mentioned limitations, which system would be capable of sorting, isolating, manipulating and preserving tagged or non-tagged cells rapidly and easily.

SUMMARY OF THE INVENTION

According to one aspect of the present invention there is provided a system for qualifying cells of a cell sample labeled with a magnetic or magnetizable moiety comprising (a) a cell sample holder for holding a cell of the cells and (b) a first cell analyzer including: (i) a magnetic field source for applying a magnetic field to the cell; and (ii) a sensor for qualifying and/or quantifying an effect of the magnetic field on the cell.

According to further features in preferred embodiments of the invention described below, the system further comprises a second cell analyzer for qualifying and/or quantifying a feature of the cell.

According to still further features in the described preferred embodiments the second cell analyzer is capable of detecting a morphological feature of the cell, a biochemical feature of the cell, a molecular feature of the cell, an electrical feature of the cell, a flow dynamics feature of the cell, a density of the cell, a membrane permeability feature of the cell and an optical feature of the cell.

According to still further features in the described preferred embodiments the system further comprises a cell manipulating device.

According to still further features in the described preferred embodiments the cell manipulating device is selected from the group consisting of an electroporation chamber, an electroporation actuator, an ultrasound actuator, a laser actuator, a radiofrequency actuator, a microwave actuator, a mechanical actuator and a thermal actuator. The cell manipulating device can also be used to introduce and/or remove a molecule from the cell.

According to still further features in the described preferred embodiments the cell manipulating device is capable of facilitating preservation of the cell or is capable of destroying the cell.

According to still further features in the described preferred embodiments the magnetic field is an electromagnetic field.

According to still further features in the described preferred embodiments the magnetic field source and the sensor are electromagnetic coils.

According to still further features in the described preferred embodiments the magnetic field source and the sensor are incorporated into a single electromagnetic coil.

According to still further features in the described preferred embodiments the first cell analyzer is capable of producing a transient magnetic field.

According to still further features in the described preferred embodiments the cell sample holder is a capillary tube.

According to still further features in the described preferred embodiments an internal diameter of the capillary tube is selected so as to restrict passage therethrough to a single cell.

According to still further features in the described preferred embodiments the magnetic field source and the sensor are each arranged around a circumference of the capillary tube.

According to still further features in the described preferred embodiments the magnetic field source is capable of generating a pulsating magnetic field.

According to still further features in the described preferred embodiments the magnetic field source is capable of generating a magnetic field of alternating polarity.

According to still further features in the described preferred embodiments the magnetic field source is capable of varying a polarity shift of the magnetic field of alternating polarity.

According to still further features in the described preferred embodiments the system further comprises a cell manipulator capable of manipulating the cell based on the effect of the magnetic field on the cell.

According to still further features in the described preferred embodiments the system further comprises a cell preservation device for preserving cells.

According to still further features in the described preferred embodiments the cell preservation device is a cryopreserver.

According to another aspect of the present invention there is provided a method of identifying cells of interest in a cell sample comprising: (a) labeling the cells of interest with at least one type of a magnetic or magnetizable moiety; (b) exposing each cell of the cell sample to a magnetic field; (c) measuring a response of each cell of the cell sample to the magnetic field; and (d) identifying the cells of interest according to the response.

According to still further features in the described preferred embodiments the response is current generated in a coil by a magnetic field of the magnetizable moiety.

According to still further features in the described preferred embodiments the method further comprises the step of analyzing at least one feature of at least a subset of cells of the cell sample prior to, during or following step (b).

According to still further features in the described preferred embodiments the at least one feature is selected from the group consisting of a morphological feature, a biochemical feature, a molecular feature, an electrical feature, a flow dynamics feature, a density feature, a membrane permeability feature and an optical feature.

According to still further features in the described preferred embodiments the method further comprises the step of manipulating cells of interest.

According to still further features in the described preferred embodiments the method further comprises the step of separating the cells of interest from the cell sample according to the response.

According to still further features in the described preferred embodiments the manipulating includes subjecting the cells of interest to an electroporation field.

According to still further features in the described preferred embodiments the method further comprises the step of cryopreserving the cells of interest.

According to still further features in the described preferred embodiments the subset of cells includes unlabeled cells.

According to still further features in the described preferred embodiments the subset of cells includes the cells of interest.

According to still further features in the described preferred embodiments the cells of interest are labeled with two types of magnetic or magnetizable moieties and whereas step (d) includes identifying of cells labeled with one type of the two types of magnetic or magnetizable moieties or with the two types of magnetic or magnetizable moieties.

According to still further features in the described preferred embodiments step (d) is effected by measuring an effect of a magnetic field generated by the at least one magnetic or magnetizable moiety on an induction coil.

According to still further features in the described preferred embodiments the magnetic field is a pulsating magnetic field source.

According to still further features in the described preferred embodiments the magnetic field is of alternating polarity.

According to still further features in the described preferred embodiments the magnetic field of alternating polarity is of varying polarity shift.

According to still further features in the described preferred embodiments the cell sample is a biological sample.

According to still further features in the described preferred embodiments the cells of interest are stem cells.

According to still further features in the described preferred embodiments the stem cells are adult stem cells.

According to still further features in the described preferred embodiments the adult stem cells are hematopoietic stem cells.

According to still further features in the described preferred embodiments the adult stem cells are mesenchymal stem cells.

According to still further features in the described preferred embodiments the cells of interest are fetal cells.

According to yet another aspect of the present invention there is provided a cell preservation device comprising a cell chamber being configured for: (a) permeabilizing a membrane of a cell; (b) introducing a cell preserving composition into the cell.

According to still further features in the described preferred embodiments the cell chamber is further configured for removing the cell preserving composition from the cell.

According to still further features in the described preferred embodiments the cell chamber is configured capable of performing step (a) and optionally (b) on a single cell.

According to still further features in the described preferred embodiments (a) is reversible permeabilization.

According to still further features in the described preferred embodiments the cell chamber includes two chambers separated by a membrane having an opening sized for trapping the cell therein.

According to still further features in the described preferred embodiments the device further includes at least one pair of electrodes flanking the membrane and whereas the membrane is fabricated from an electrically insulative material.

According to still further features in the described preferred embodiments the electrically insulative material is silicone nitride.

The present invention successfully addresses the shortcomings of the presently known configurations by providing a system capable of sorting cells of a mixed cell population as well as manipulate, genetically modify and cryo preserve such cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
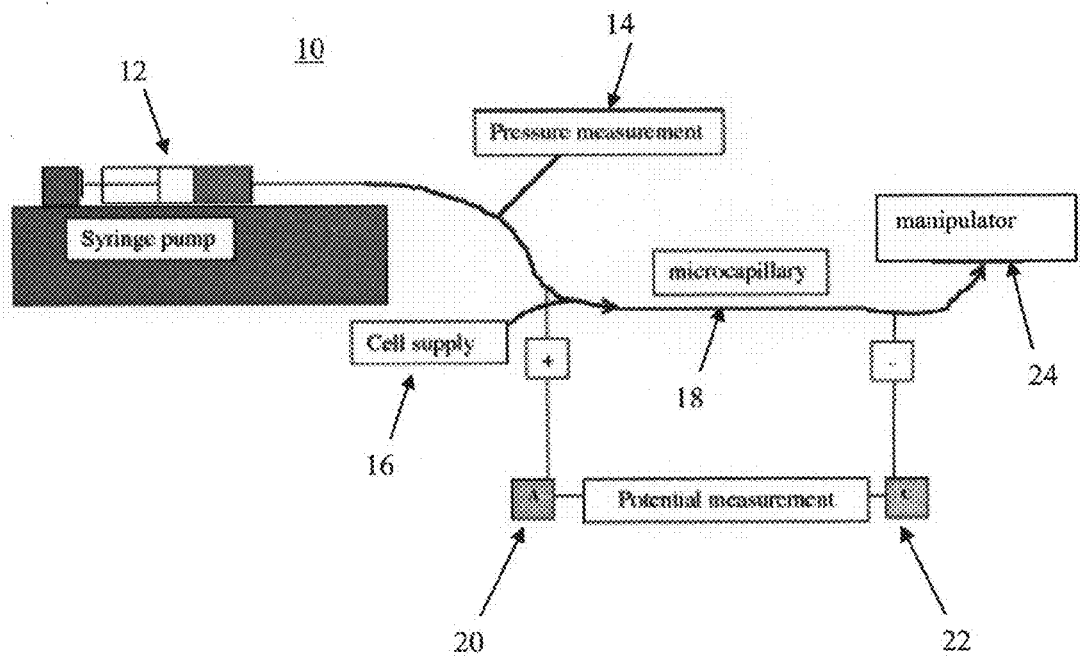

FIG. 1 schematically illustrates one embodiment of the system of the present invention.

Figure 2:
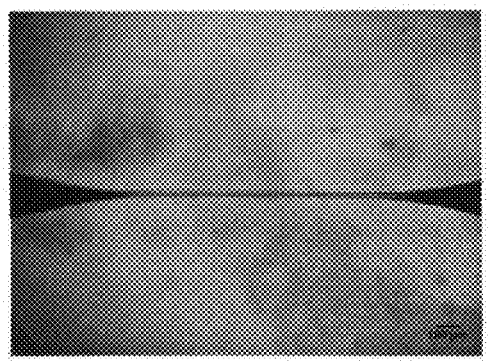
Figure 3:
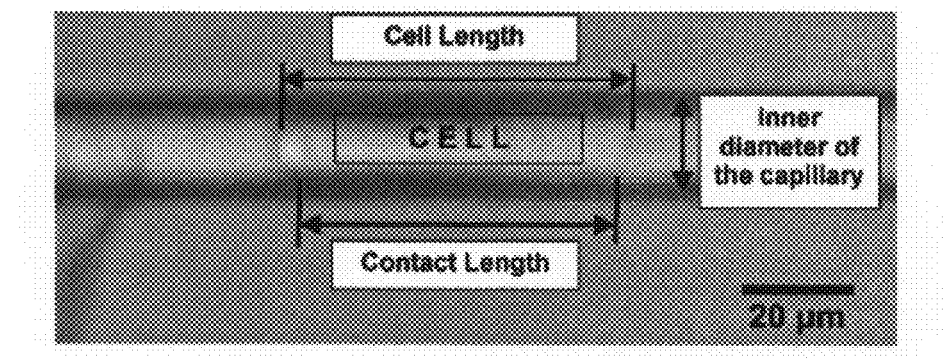

FIG. 2 is a microscope image of a microcapillary tube suitable for use with the present invention FIG. 3 is a microscope image showing a single cell occupying the microcapillary tube of FIG. 2.

Figure 4:
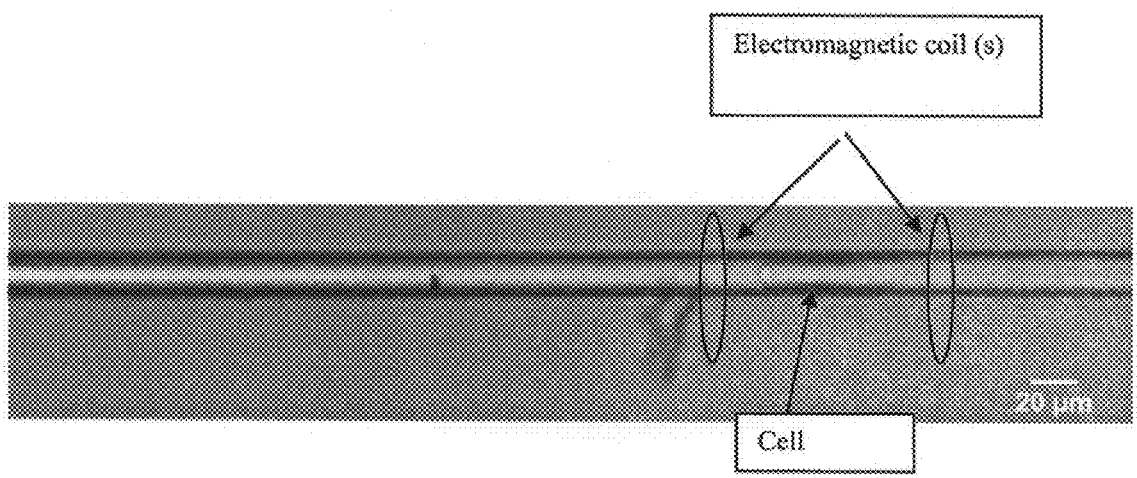

FIG. 4 illustrates placement of the electromagnetic coils around the microcapillary tube of the system of the present invention.

Figure 5:
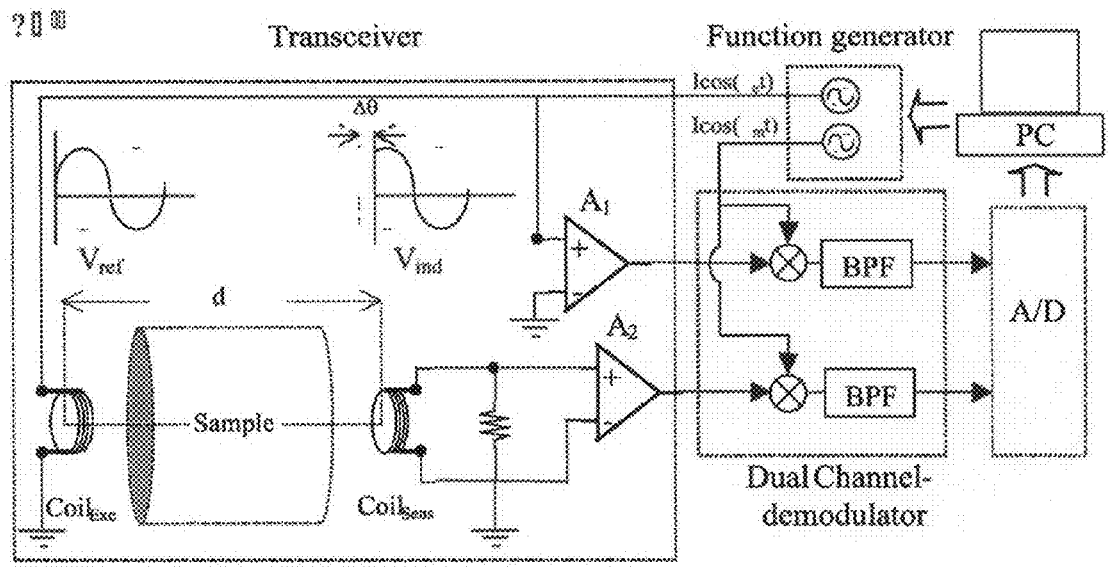

FIG. 5 schematically illustrates circuitry, which can be used to construct the cell detector component of the system of the present invention.

Figure 6:
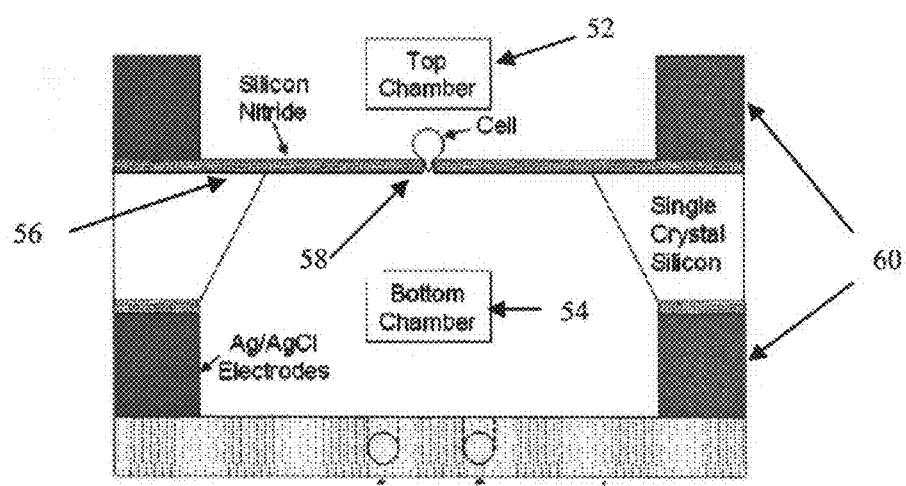

FIG. 6 schematically illustrates one embodiment of a cell preservation device constructed in accordance with the teachings of the present invention.

Figure 7:
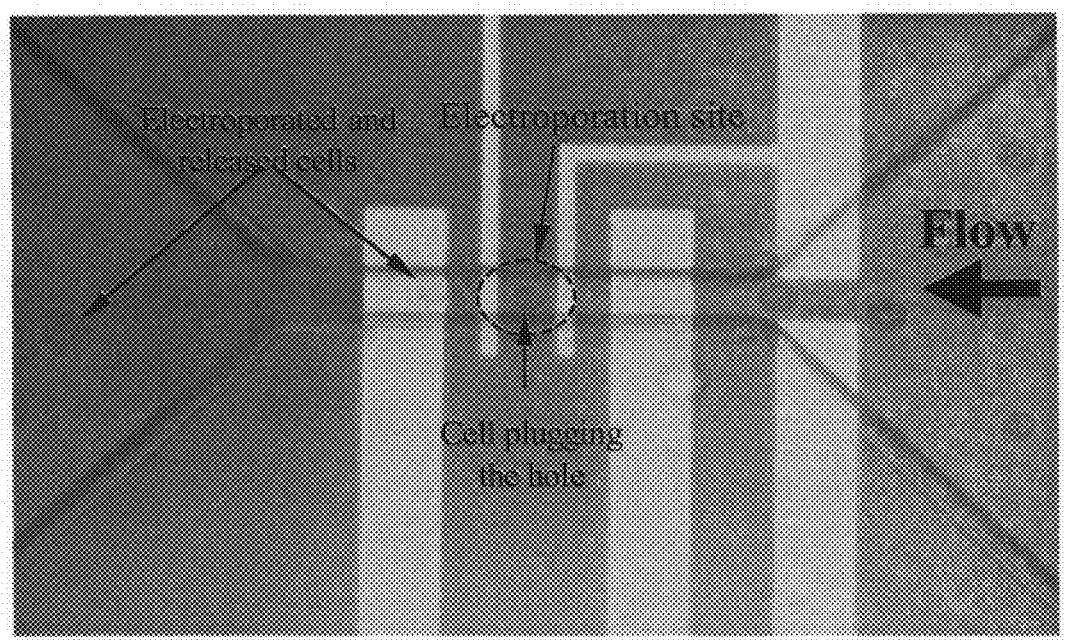

FIG. 7 illustrates another embodiment of a cell preservation device constructed in accordance with the teachings of the present invention.

Figure 8:
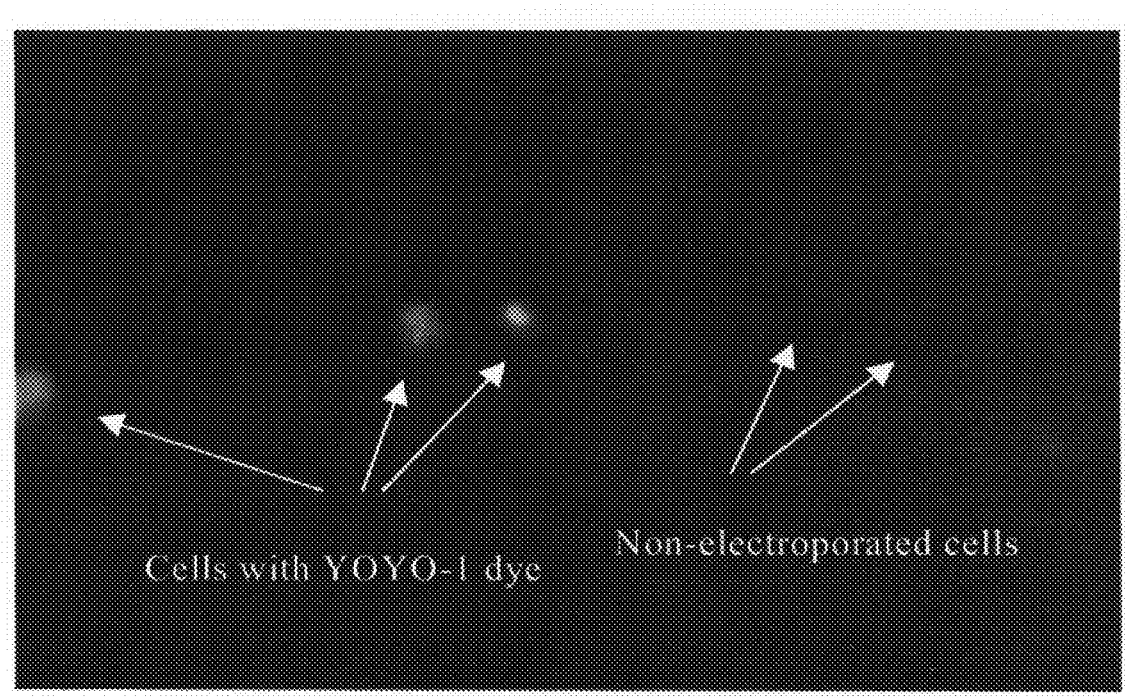

FIG. 8 is a fluorescent image of cells stained with a fluorescent dye following single cell-electroporation in micro channels.

Figure 9:
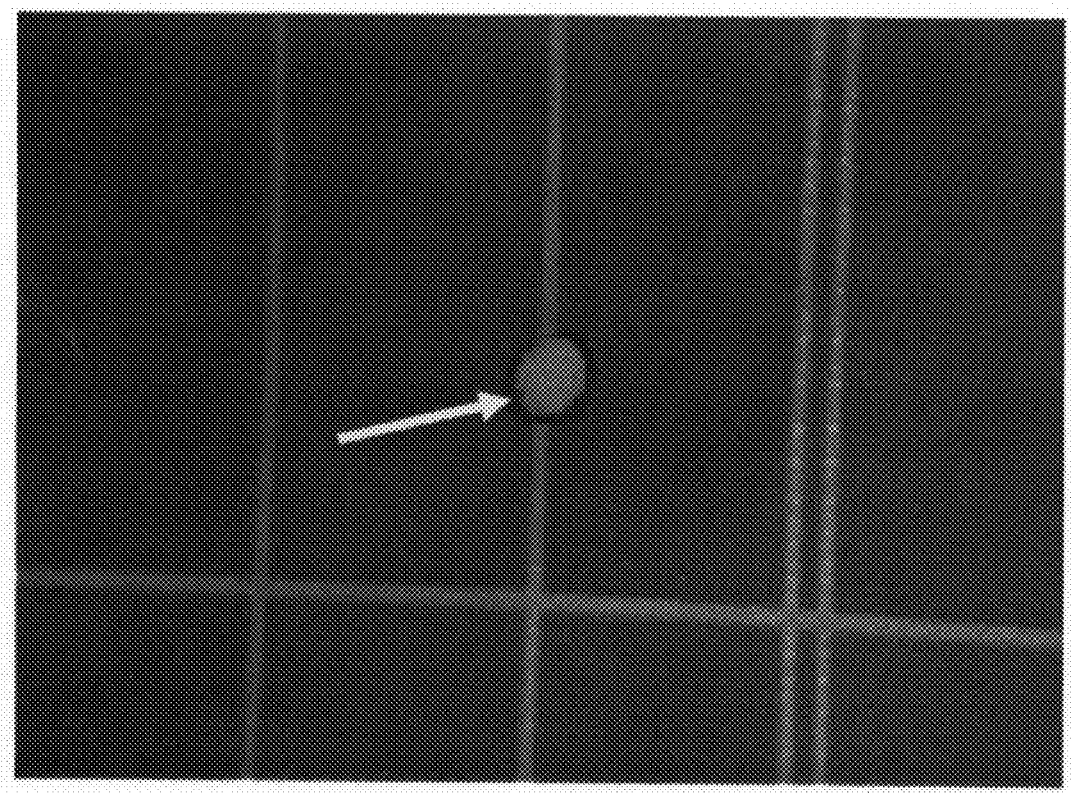

FIG. 9 is a fluorescent image of cells stained with a fluorescent dye following single cell-electroporation in micro capillaries.

DESCRIPTION OF THE PREFERRED EMBODIMENTS

The present invention is of a system and method, which can be used to sort, manipulate and preserve cells of a mixed cell population. Specifically, the present invention can be used to sort, transform and preserve individual cells of a mixed population of cells.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Systems for sorting and isolating specific cell types are well known in the art. Although such systems are typically efficient in sorting mixed cell populations, they are oftentimes expensive and difficult to operate and lack in-line capabilities of cell engineering or manipulation and preservation features.

While reducing the present invention to practice, the present inventors devised a cell sorting system that relies in part upon magnetic induction for cell identification while incorporating features such as additional cell manipulation modalities and in-line cell preservation which are absent from prior art systems.

Thus, according to one aspect of the present invention there is provided a system for qualifying cells of a cell sample labeled with a magnetic or magnetizable moiety.

The system of the present invention includes a cell sample holder for holding a cell; and a cell analyzer which incorporates: (i) a magnetic field source for applying a magnetic field to the cell and (ii) a sensor for qualifying and/or quantifying an effect of the magnetic field on the cell.

The cell holder can be any device capable of holding a cell under a magnetic field. Preferably, the cell holder is constructed such that a single cell is exposed to the magnetic field at a time. One example of such a cell holder is the microcapillary tube described in Example 1 of the Examples section. Additional cell holder configurations can include porous microbeads, which can accommodate a single cell at a time, single cell chambers, or channels.

The magnetic field can be applied by a permanent magnet (e.g. a neodymium magnet) or by an electromagnet of direct or alternating current. As is further described hereinbelow, the use of an electromagnet is presently preferred.

As used herein, the term "magnetizable moiety" denotes any material, which is characterized by electrically conductivity and/or a capability of being magnetized (further description of properties can be found in Example 4). Examples of magnetizable materials include ferromagnetic or paramagnetic materials such as iron, iron oxide, gadolinium, or gold.

In order to sort cells of a mixed cell population, a cell sample labeled with cell-specific tags which include a magnetic or magnetizable moiety (see further description in Table 1) is loaded into the cell holder and each individual cell is exposed to the magnetic field and the effect of such a field on the cell is measured thus enabling characterization of the magnetic properties of the cell. A more detailed description of cell sorting and isolation using the present system is provided hereinbelow and in the Examples section which follows.

Thus, in its simplest configuration, the present system enables discrimination between cells labeled with a tag having a magnetic or magnetizable moiety and non-labeled cells.

The effect of the magnetic field on the cell can be measured through a change in cell morphology (e.g. a change in the cell shape), a change in cell's direction of flow, a change in cell velocity (e.g. tagged cells flow at different velocities than non-tagged cells) or a change in the electromagnetic field around the cell.

Such an effect can be measured using devices well known in the art. For example, morphological changes in the cell induced by the presence of a magnetic field can be measured using an optical scanning device such as a microscope, while cell movement/flow can be measured optically or through flow measuring devices (e.g. flow pressure transducer).

Preferably, the effect on the cell is measured via induction of current by the magnetic or magnetizable moiety of the cell tag.

The present system can employ one of several detector configurations for detecting current induction.

For example, a permanent magnet can be used to generate a transient magnetic field around the cell holder (by mechanically moving the magnet adjacent to and away from the cell holder) and the effect of this field can be measured by an induction coil positioned in proximity to the cell holder and away from the magnet.

Alternatively, a cell of the cell population can be loaded into a capillary tube surrounded by an induction coil and a current produced in the coil can be measured and used to determine the absence or presence of a cell tag having a magnetic moiety.

In a preferred configuration, the present system employs a detector utilizing two electromagnetic coils (see Example 4 of the Examples section hereinbelow).

In such a configuration, the present system employs a first (transmitter) coil which carries an electrical current and a second (receiver) coil which acts as an 'antenna' to pick up and amplify electrical currents generated by the moiety of the cell tag, which in this case is preferably magnetizable (e.g. paramagnetic). The current moving through the first coil creates an electromagnetic field. The magnetic field interacts with the magnetizable moiety of the cell tag causing the moiety to generate a weak magnetic field.

The second coil is sensitive to the magnetic fields of the magnetizable moieties and detects changes produced by the presence of the magnetizable moiety on the cell. Therefore, when the second coil is exposed to the magnetic field of the moiety, a small variation in the electric current that travels through the coil occurs. The coil amplifies the signal and sends it to an analyzer. The analyzer compares the current transmitted by the first coil and the current generated in the second coil and determines if the cell present in the cell holder is labeled with the tag. Further description of the electrical circuitry of the coils and detector is provided in Examples 1 and 4 of the Examples section.

The first coil can carry a direct current or an alternating current. An alternating current is advantageous in that it facilitates generation of magnetic fields of alternating polarity. Magnetic fields of predetermined alternating polarity can be used to further reduce background noise (in the second coil), which can arise, from cells and solutes (ions) present in the cell holder.

A magnetic field of alternating polarity can also be used to distinguish between different magnetizable moieties and thus use thereof in the present system can be beneficial since it enables concomitant use of tags having more than one type of magnetizable moieties, which vary in both inductance and resistance. By utilizing a phase modulator and a magnetic field of alternating polarity, the present system can examine the amount of phase shift and compare it with the average for a particular type of substance. The present system can discriminate cells, which produce a certain phase-shift level or fall within a certain phase shift segment.

The above described configuration can also be realized using a single coil which functions in both transmitting the electromagnetic filed to the cell and receiving an induced magnetic field from the magnetic field generated in the magentizable moiety of the cell tag.

Such a system configuration can use a single AC coil as both transmitter and receiver. The coil transmits short bursts (pulses) of current, with each pulse generating a brief magnetic field. When the pulse ends, the magnetic field collapses very suddenly, resulting in a sharp electrical spike. This spike lasts a few microseconds (millionths of a second) and causes another current to run through the coil. This current is called the reflected pulse and is extremely short, lasting only about 30 microseconds. Another pulse is then sent and the process repeats.

When the magnetic pulse hits a cell tag it creates an opposite magnetic field in the magnetizable moiety of the tag. When the pulse's magnetic field collapses, causing the reflected pulse, the magnetic field of the tag extends the reflected pulse's duration, in effect creating a magnetic echo.

A sampling circuit in the detector is set to monitor the length of the reflected pulse. By comparing it to the expected length, the circuit can determine if another magnetic field has caused the reflected pulse to take longer to decay. If the decay of the reflected pulse takes more than a few microseconds longer than normal, there is probably magnetizable object (moiety) interfering with it.

The sampling circuit sends the weak signals that it monitors to an integrator. The integrator reads the signals from the sampling circuit, amplifying and converting them to direct current (DC). The direct current's voltage is connected to a readout circuit, which indicates identification of the cell as a labeled cell.

The above described configurations are advantageous over prior art cell sorters (e.g. the Baxter ISOLEX™ 3000 System) which typically apply an external electromagnetic field to a cell population to manipulate a group of labeled cells. This leads to an effect on either the flow pattern of the labeled cells within a group of cells or in the position of the cells within the group. Thus in prior art systems labeled cells are treated as part of a group and the separation is a statistic process with variable yield. In contrast our methods deal with the effect of magnetic fields on each individual cell.

Indeed, a clinical study that analyzed the Baxter ISOLEX™ 3000 System cell sorter concluded that "The yield was still poor . . . and further optimization of the technique for clinical grade cell selection is warranted" (Bjorkstrand, B., et al., A controlled comparison of two different clinical grade devices for CD34+ selection of autologous blood stem cell grafts. J of Hematotherapy, 1999. 8: p. 75-8). Specifically, the median yield in the Baxter device was 48%".

By treating each cell individually, the present system can greatly increase sorting efficiency and yield.

The present system can be used to sort desired cells of any type of cell sample, provided that desired cells can be specifically labeled by one or more tags. Examples of cell samples, which can be sorted using the system of the present invention are those obtained from bone marrow, adipose tissue, peripheral blood, cord blood, spleen and more.

Any type of cell specific label, which is modified to include a magnetic or magnetizable moiety can be utilized by the present invention. Typically, a cell receptor ligand or antibody attached to a particle nanometer to micrometers in size is utilized for cell labeling.

Magnetic or magnetizable tags are commercially available or can be prepared using well-known methodology (see, for example, Monoclonal Antibodies, CRC Press, Paul M. Vanhoutte, Zola Zola, Heddy Zola, 1987. Table 1 below provides examples of tags, which can be used by the present invention.

TABLE 1

| Cell marker | For the specific isolation of: | Source |
|---|---|---|
| CD105 | Mesenchymal Stem Cells | Multenyi Biotec |
| CD34 | Hematopoeitic stem cells | Multenyi Biotec |
| CD56 | NK Cells | Multenyi Biotec |
| CD3 | T cells | Multenyi Biotec |
| TCRγ/δ | TCRγ/δ cell | Multenyi Biotec |
| CD8 | T cytotoxic cells | Multenyi Biotec |
| CD4 | T helper cells | Multenyi Biotec |
| CD4; CD25 | T regulatory cells | Multenyi Biotec |
| CD 19, 20, 22 | B Cells | Multenyi Biotec |
| CD304 | Plasmacytoid dendritic cells | Multenyi Biotec |
| CD141(BDCA-3) CD1c(BDCA-1) | Myeloid dendritic cells | Multenyi Biotec |
| CD14, 11b | Moocytes/ Macrophages | Multenyi Biotec |
| CD16 | Neutrophils, Eosinophils | Multenyi Biotec |
| CD15 | Granulocytes | Multenyi Biotec |
| CD61 | Megakaryocytes, Platelets | Multenyi Biotec |
| CD71 | Erythrobalsts, | Multenyi Biotec |
| CD235a | Erythrocytes | Multenyi Biotec |

To label a cell type of interest, cells of the cell population are exposed to the tag by mixing the cell population with the cell tag under conditions suitable for cell specific binding of the cell tag. For example, in the case of a CD105-specific tag a cell suspension is prepared from bone marrow aspirates or enigmatically digested adipose tissue. Dead cells are removed using Ficoll gradient and cell clumps are disaggregated/removed using a nylon mesh filter. $10^7$ cells are suspended in 80 μl of PBS-BSA-EDTH buffer and then 20 μl of CD105 coated microbeads are added to the cells. The cell population can then be introduced into the cell holder of the present system (in a manner similar to that described in Example 1) and the cells individually examined and sorted.

The system of the present invention also includes a cell manipulating device. As used herein, the phrase "cell manipulating device" refers to any device capable of physically manipulating a cell (e.g. changing cell flow, moving the cells), chemically or genetically modifying the cell (e.g. introducing a composition onto or into the cell, freezing or heating the cell, desiccating the cell and the like).

Examples of a cell-manipulating device include, but are not limited to, an electroporation device, an ultrasound actuator, a laser, a radiofrequency actuator, a microwave actuator, a mechanical actuator and a thermal actuator.

Specific examples of such devices include systems for detecting cell viability (Y. Huang, N. Sekhon, J. Borninski, N. Chen, B. Rubinsky, "Instantaneous, quantitative single-cell viability assessment by electrical evaluation of cell membrane integrity with microfabricated devices," *Sensors and Actuators*. A Vol (105)/1 pp 31-39, 2003).

Use of an electroporation-capable cell-manipulating device is presently preferred. An in-line electroporation device can be realized by placing a pair of electrodes around the cell holder as is exemplified by Example 2 of the Examples section, which follows. Alternatively, a dedicated chamber fluidly connected to the cell holder can be used to electroporate sorted cells (Rubinsky, B. "Microelectroporation for cellomics" in *Lab on Chips for Cellomics*, Eds. H. Andersson and A. van den Berg, Kluwer Academic Publ. Dordrecht, pp 123-143, 2004).

An electroporation device can be used to introduce a composition into the cell following or during cell sorting. Such a composition can be used to destroy the cell or to preserve the cell (e.g. cryopreservant). The composition can also be used to chemically or genetically modify the cell. Examples of compositions that can be electroporated into the cell include, but are not limited to, polynucleotides (e.g. plasmids, siRNA, oligonucleotides), polypeptides (e.g. cytokines, anti apoptotic agents, growth hormones) small molecules (e.g. anti cancer drags, fluorescent dyes), crypreservants (e.g. DMSO, glycerol).

Further description of cell preservation is provided hereinbelow and in Examples 2-3 of the Examples section which follows.

Although cell sorting using the magnetic induction properties of cell tags can be used to detect labeled cells, in order to efficiently distinguish and separate labeled cells from the cell population there is a need for a minimum of two different types of cell analyzers.

The first cell analyzer needs to be sensitive to the label moiety, e.g. the magnetic induction analyzer described above, while the second cell analyzer needs to be capable of detecting every cell flowing within the cell holder or alternatively only the cells not labeled with the magnetic or magnetizable moiety.

There are several detection systems that can detect every type of cell, in the confinement of the cell holder. Examples include optical systems such as a CCD camera or laser monitoring or fluorescence monitoring, ultrasound systems, electrical systems capable of detecting currents through the cell holder (in a specific frequency domain) and flow measurement systems capable of measuring velocity or pressure in the cell holder.

Measurements obtained from such additional cell analyzers can be superimposed on top of the magnetic induction measurements describe above to provide a composite cell analysis image.

Thus, to further enhance cell sorting, the system of the present invention preferably also includes a second cell analyzer. The second cell analyzer is capable of detecting a morphological feature of the cell, a biochemical feature of the cell, a molecular feature of the cell, an electrical feature of the cell, a flow dynamics feature of the cell, a density of the cell, a membrane permeability feature of the cell and an optical feature of the cell.

Examples of such an analyzer include, but are not limited to, optical flow cytometry, FACS, electrical flow cytometry by Coulter.

Thus, this embodiment of the present system enables analysis of at least two features of each individual cell as it flows through a cell holder (e.g. microcapillary).

This added cell analysis feature of the present system greatly enhances cell sorting and clearly distinguishes the present system from prior art systems such as that disclosed in U.S. Pat. No. 6,597,176.

The system of U.S. Pat. No. 6,597,176 relies upon magnetic induction to detect the presence or absence and quantity of ferromagnetic particles, which can be attached to cells; this system cannot detect cells, which are not labeled. Since typical cell sorting applications require that each individual cell marked with particles be separated from those that are not in order to selectively manipulate cells of a mixed cell population, efficient separation requires the identification of labeled and non-labeled cells at the single cell level, such that each cell is manipulated in a different manner (e.g. retain labeled cells and discard non-labeled cells or vice versa).

Additional cell analysis features that enable identification of each cell of the cell population (whether labeled or not) are not available in prior art systems such as that described in U.S. Pat. No. 6,597,176.

A primary goal of the present system is to separate and manipulate the labeled cells differently from those that are not labeled. When cross correlation between the different cell analyzers indicates that a specific cell is labeled, the cell manipulator is utilized to treat the cell in a specific manner (e.g. direct the cell into a cell preserving device). This concept can be also applied in reverse with undesirable cells being labeled with the tag and manipulated in a specific manner (e.g. ablated and destroyed).

A preferred embodiment of the present system includes a magnetic induction analyzer coupled with a second cell analyzer for measuring electrical impedance of a cell. The presence of a cell in the channel will change the electrical impedance between the electrodes. When cross correlation shows that this cell also possess a magnetic or magnetizable tag, the electrodes can be used to apply a pulse that results in electroporation of the cell in order to introduce a desirable substance in the cell.

It will be appreciated that since cell sorting typically leads to subsequent cell isolation and manipulation, and since some cell types require preservation Several cell preserving configuration can be implemented in the present system.

Preferably, the cell-preserving device utilizes electroporation of cells in the presence of a cryopreservant to preserve selected cells.

Electroporation is a phenomenon that makes cells permeable by exposing them to strong, rapid electric pulses (43. Weaver, J. C., and Y. A. Chizmadzhev. Theory of electroporation: a review. *Bioelectrochem. Bioenerg.* 41: 135-160, 1996). It is commonly used in medicine and biotechnology for the introduction of non-permeable chemical species across the cell membrane, from small molecules such as fluorescent dyes, drugs and radioactive tracers to high molecular weight molecules such as antibodies, enzymes, nucleic acids, dextrans and DNA.

Once a cell is permeabilized, transport across the membrane is primarily dictated by the size of the molecule; small molecules generally enter via diffusion and larger molecules require electrophoretic forces from subsequent pulses to enter the cell. The effect of electrical pulses on the cell membrane depends on several electrical pulse parameters, such as pulse amplitude, shape, and length repetition rate. As a function of these various parameters, the electroporation pulse can either have no effect on the cell membrane, reversibly open the cell membrane or irreversibly open the cell membrane.

Cryopreservation, the preservation of biological materials by freezing is now a common approach in biotechnology and medicine. Freezing is used for storage of biological materials since low temperatures slow biochemical reactions. The mechanisms involved in cryopreservation of biological materials were thoroughly explored during the last century, and are presented in numerous studies (Fahy G M, Wowk B, Wu J. Cryopreservation of complex systems: the missing link in the regenerative medicine supply chain. Rejuvenation Res. 2006; 9(2):279-91).

Such studies have uncovered that survival of cells preserved at low temperatures (e.g. in liquid nitrogen) depends on the cooling rate during freezing which follows a U shaped curve, with optimal survival achieved at a particular rate of cooling and survival decreasing at higher and lower cooling rates. It has been found that chemicals such as Dimethyl sulfoxide and glycerol can improve cell survival during freezing at suboptimal cooling rates when introduced into the cell by diffusion through the cell membrane. The preservation mechanism is achieved by dilution of the intracellular ionic composition. However, since cryoprotectant chemicals can be toxic to the cell and thus when designing cryopreservation protocols, the p cryopreservant, its concentration and the mode of introduction thereof into cells and removal from the cells play an important role. The cryoprotectant commonly used for cell cryopreservation is Dimethyl sulfoxide (Me2SO). Me2SO can cause a variety of mild to moderate side effects including nausea, vomiting, and diarrhea (Davis, J. M., S. D. Rowley, et al. (1990). "Clinical toxicity of cryopreserved bone marrow graft infusion." Blood 75: 781-786. Me2SO also can induce histamine release and cause side effects that range in severity from rashes and flushing to hypotension, bronchospasm, pulmonary edema and respiratory compromise Hypertension may result from the effect of Me2SO on smooth muscle (Davis, Rowley et al. 1990 *Ibid*). The second reason for complications resulting from cryopreservation is related to damage of cells during the cryopreservation and thawing process. Lysis of cells results in cell debris and cell aggregates which can lead to pulmonary emboli (Fautsch et al. 1991, *Ibid*). Children undergoing chemotherapy are considered to have reduced circulatory and renal reserves and may be at increased toxicity risk due to marrow infusion [Okamoto, Y., Y. Takaue, et al. (1993). "Toxicities associated with cryopreserved and thawed peripheral blood stem cell autografts in children with active cancer." Transfusion 33: 578-581]. Attempts to remove DMSO or unwanted dead cells following thawing of marrow have been largely unsuccessful due to technical difficulties. In addition, such methods have been clinically ineffective in reducing side effects of marrow infusion [Stroncek, D. F., S. K. Fautsch, et al. (1991). "Adverse reactions in patients transfused with cryopreserved marrow." Transfusion 13(6): 521-526].

Thus, two main parameters affect successful cryopreservation, controlled and optimal cooling rates and controlled and optimal introduction and removal of cryoprotectant chemicals from cells.

While further reducing the present invention to practice, the present inventors have realized that a cell sorting system would benefit from an in-line cell preserving device which is capable of introducing a cryopreservant into selected cells and is further capable of efficiently removing such a cryopreservant from the cell.

Thus according to another aspect of the present invention there is provided a cell preservation device which is capable of preserving individual cells. It will be appreciated that although the cell-preserving device of this aspect of the present invention finds use in the present system, it can also be adapted for use with any cell sorting or manipulating device.

The cell preserving device of the present invention includes a cell chamber which is configured for permeabilizing a membrane of a cell and introducing a cell preserving composition into the cell.

Several configurations of the cell chamber can be utilized by the cell preserving device of the present invention provided such configurations enable electrophoretic manipulation of a cell membrane of a single cell.

One preferred embodiment of a cell chamber is described in Example 2 of the Examples section, which follows. Such a chamber configuration employs two chambers (or a split chamber) separated by a non-conducting membrane (e.g. silicon nitride) having an opening sized and configured for trapping a single cell therein. Such an opening can be a circular hole having a diameter ranging from several hundred nanometers to several hundred microns depending on the cell targeted from electroporation. For example, in the case of CD105+ Mesenchymal Stem Cells, such an opening has a diameter of about 5 microns.

The chambers are fitted with electrode pairs, which generate a an electrical field which is focused at the cell membrane since the cell represents the only conductive path through the membrane. As is described in more detail in the Examples section, such a current permeabilizes the cell membrane and enables introduction of a cryopreservant present in one of the chambers into the cell. The magnitude and pattern of the current generated by the electrodes depends on the cells electroporated and the cryopreservant type. In general electrical fields that produce reversible electroporation range from 200 V/cm to 500 V/Cm and the application time is from 100 microsecond to 1000 microseconds.

The cell preservation device further includes a cooling and optionally heating device which functions in freezing the cells following introduction of the cryopreservant. Examples of such a device include Peltier cooling system. Such a device can function at the single cell level or on a group of cells. In any case, electroporated cells can be frozen directly in the cell chamber or in a second dedicated chamber.

Cell freezing is preferably effected on single cells via a directional solidification approach. Single cells are set upon a thermally conductive substrate and freezing is performed by controlling the temperature of the substrate and the positioning of the cells on the substrate. For further detail on directional solidification, please see U.S. Pat. No. 4,531,373.

Thus, the present cell preservation device enables single cell cryopreservation. It will be appreciated that an added advantage of a device, which is capable of electrophorating single cells, is efficient removal of a cryopreservant from the cells.

Since cryopreserved cells are likely to be used in subsequent human or animal therapy (see below), efficient and complete removal of the cryopreservant without damaging the cell is highly desirable. Thus, the present cell preservation device is also configured capable of removing the cryopreservant from individual cells.

To effect such removal, the cell is again trapped within the opening of the membrane and the electrophoresis field is reversed with the same parameters and time as during the introduction of the cryoprotectants. As is mentioned hereinabove, cell sorters find use in various applications including research, diagnostics and therapeutics.

Thus, the present system can be utilized in various diagnostic procedures, including, for example, identification of fetal cells in maternal blood or identification of pathogenic cells in a tissue or blood sample.

For example, sorting of cell samples derived from tissue and isolation and optionally cryopreservation of potentially tumorous cells can represent a first step to cell characterization and diagnosis [e.g. detection of circulating cancer cells in the peripheral blood: Baran J, Pituch-Noworolska A, Krzeszowiak A, Wieckiewicz J, Stachura J, Pryjma J, Popiela T, Szczepanik A, Zembala M. Detection of cancer cells in the blood by FACS sorting of CD45-cells. Int J Mol Med. 1998 March; 1(3):573-8. Pituch-Noworolska A, Wieckiewicz J, Krzeszowiak A, Stachura J, Ruggiero 1, Gawlicka M, Szczepanik A, Karcz D, Popiela T, Zembala M. Evaluation of circulating tumour cells expressing CD44 variants in the blood of gastric cancer patients by flow cytometry. Anticancer Res. 1998 September-October; 18(5B):3747-52. Martin VM, Siewert C, Scharl A, Harms T, Heinze R, Ohl S, Radbruch A, Miltenyi S, Schmitz J. Immunomagnetic enrichment of disseminated epithelial tumor cells from peripheral blood by MACS. Exp Hematol. 1998 March; 26(3):252-64].

Cells, and in particular adult stem cells find increasing use in cell therapy of animals and humans. One of the major hurdles of using such cells is efficient isolation thereof from tissue samples.

This problem is compounded by the fact that adult stem cells are present in minute amounts in tissue. For example, mesenchymal stem cells and hematopoietic stem cells, which are increasingly used and investigated as the cells of choice for various cell replacement therapies represent only 0.01% of cell in bone marrow. Such cells are currently utilized in horses and other animals as skeletal cell progenitors for repair of injured tendons, ligaments and bone (Stephen Picock, Stem Cells in Race Horses, The Scientist, October 2005:34-35), while in humans, mesenchymal stem cells find use in repair of skeletal and myocardial disorders, such as non-union fractures, cartilage defects in Osteoarthritis, tendon tears and myocardial infarcts [Gafni et al. Stem cells as vehicles for orthopedic gene therapy. Gene Ther. 2004 February; 11(4):417-26; Minguell J J and Erices A. Mesenchymal stem cells and the treatment of cardiac disease. Exp Biol Med (Maywood). 2006 January; 231(1):39-49.], while hematopoietic stem cells find use in cell replacement therapy following, for example, chemoablation.

Thus, there is a need for efficient isolation of such cells from tissue samples. The present system addresses such needs by enabling efficient sorting and isolation of cells from cells samples while also enabling in-line preservation of isolated cells thus increasing the effective life span and suitability-for-use of such cells.

It will be appreciated that although the present invention was described in context with identification and isolation of cells, that it can also be utilized to identify and isolate molecules of interest, e.g. polynucleotides, polypeptides and the like using molecule-specific probes labeled with magnetic or magnetizable moieties.

It is expected that during the life of this patent many relevant cell tags will be developed and the scope of the term cell tag is intended to include all such new technologies a priori.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Cell Sorting Using Cell Labels Having Magnetizable Particle Moieties

The present system is designed for identifying and separating specific cells labeled with magnetic particles. The embodiment of the present system illustrated in the following example employs several components (shown in FIGS. 1-5): (i) a microcapillary tube restricting flow to single cells; (ii) induction coils for generating an electromagnetic field around the microcapillary tube; (iii) micro channels through which selected cells flow; and (iv) electroporation electrodes for introducing various compounds (e.g. polynucleotides, cryoprotectants etc) into cells flowing through the microchannels.

As is shown in FIG. 1 the present system employs a constant flow device (which in this case is represented by a syringe 12 and pressure measurement device 14) that introduces cells from a cell supply 16 into a microcapillary tube 18. Flanking the cell-containing region of the microcapillary tube are two electromagnetic coils (indicated by 20 and 22) which are utilized to detect the presence of a cell carrying magnetic particles. Cells that are positively identified are sorted using a cell manipulator 24.

Preferably, the microcapillary tube is constructed having an inner diameter which forces single cells to pass therethrough (FIG. 2). A single cell occupying the microcapillary tube is shown in FIG. 3.

FIG. 4 illustrates one possible configuration for detecting the electromagnetic field perturbation produced by the presence of a cell labeled with paramagnetic particles. Systems, which employ one coil, are also envisaged, as is further described hereinabove. The two coils surround the microcapillary, with the cell flowing between them. Because biological solutions are ionic, generating an electrical current in one of the coils produces an induction current in the second coil. The presence of a magnetized cell between the coils will cause a change in the induced current. Such a change varies in magnitude between cells labeled with magnetic/magnetizable particles and cells that are not, thus leading to detection of labeled cells. The principle of magnetic induction and the use thereof in identifying cell labeled with magnetic/magnetizable particles are further explained in the preferred embodiments section above.

FIG. 5 illustrates typical circuitry that can be used to detect the presence of a cell positioned between the coils. The system shows a multi-frequency inductive spectrometer. The system consists of four modules: function generator, transceiver, dual-channel demodulator and analog-digital converter. A personal computer with a PENTIUM™ 2GHz processor (model 4400, Dell Inc. Round Rock, Tex.) controls the system and processes the data. The function generator module uses two identical programmable synthesizers NI 5401 (National Instruments Inc, Austin, Tex.) as oscillators. The first oscillator supplies an excitation signal I $\cos(\omega_e t)$ of approximately 20 mA in the range of 1 to 8 MHz at pre-programmed steps. A modulation signal $I\cos(\omega_m t)$ is generated by the second oscillator. The difference $\omega_e - \omega_m = \omega_o = 100(2\pi)$ rad/sec is maintained constant in the whole bandwidth in order to produce a narrow band measured voltage signal on a constant low intermediate requency for processing and demodulation.

The excitation and modulation signals are connected to the transceiver and the dual-channel demodulator modules respectively. The transceiver consists of an excitation and a sensing coil coaxially positioned and two differential receiver amplifier AD8130 (Analog Devices Inc. Norwood, Mass.) (A1 and A2). Both coils can be built using magnet wire AWG32 rolled on a cylindrical plastic former with radius r=2 cm, and five turns. The coil inductance of such coils, as calculated on the basis of Faraday's law, is approximately 40 µH. The excitation coil generates a primary oscillating magnetic field. The sensing coil detects the primary magnetic field and its perturbation through a proximal conductive sample. To avoid inductive pickup the leads of the coils are twisted. The amplifiers A1 and A2 were connected as conventional operational amplifiers and collect the reference voltage ($V_{ref}$) and the induced voltage ($V_{ind}$) in the excitation and sensing coils respectively. The gain of the amplifiers was adjusted in order to obtain a dynamic range of ±5V throughout the whole bandwidth.

The dual-channel demodulator module uses a mixer and a narrow band pass filter to transfer the information of any excitation and sensing signal of a variable frequency to a constant low frequency ($\omega_o$). The multiplier AD835 (Analog Devices Inc. Norwood, Mass.) was used as mixer. And the narrow band pass filter was designed on the basis of the operational amplifier AD844 (Analog Devices Inc. Norwood, Mass.). This module uses two identical channels for parallel demodulation. To avoid additional inductance and stray capacitance in the circuit, the amplifiers and dual channel-demodulator circuits are shielded by a metallic box and connected to the coils with short coaxial cables (length less than 0.8 m). The current passes through the shield to minimize any inductance mutual between the circuit and the coils.

The analog-digital conversion module digitizes the reference and induced voltage signals on the constant low frequency. A data acquisition card NI 6071E (National Instruments Inc, Austin, Tex.) with a sample rate of 1.25MSamples/seg and a resolution of 12 bits is used as an analog-digital converter. The phase of the reference and induced voltages are calculated in software over approximately five cycles by an extract single tone function available in LABVIEW V6.1 (National Instruments Inc, Austin, Tex.). This function can be programmed to find the highest amplitude at $100(2\pi)$ rad/sec and return the phase. The phase shift between the reference and induced voltage was estimated as $\Delta\theta = \theta(V_{ind}) - \theta(V_{ref})$. The ratio signal to noise (SNR) for phase shift measurement was improved by averaging over twenty spectra (39 dB at 1 MHz). Thus, cells labeled with magnetic/magnetizable particles have a different affect on inductive transfer between the coils than cells not labeled with magnetic/magnetizable particles.

Example 2

Cryopreservation of Sorted Cells Using a Single Cell Micro-electroporation System FIGS. 6-7 illustrate one embodiment of a cell preservation device constructed in accordance with the teachings of the present invention.

As is illustrated in FIG. 6, cell preservation device 50 includes a top chamber 52 and a bottom chamber 54 separated by an electrically insulating and transparent silicon nitride membrane 56. The membrane is 1 micron thick and has a 2-5 micron opening 58 in the middle. The membrane is flanked by circular Ag/AgCl electrodes 60.

Chambers 52 and 54 are designed capable of maintaining a temperature from 0° C. to 42° C. by employing, for example, Peltier cooling plates. Single cells can be trapped in opening 58 (FIG. 7) by generating a hydrostatic pressure differential between chambers 52 and 54. An alternative configuration can employ a capillary tube (similar to that shown in FIGS. 1-5), which is flanked by electroporation electrodes rather than coils (see Example 3 below).

Such a micro-electroporation setup can be used for introducing a composition of interest (e.g. polynucleotides, polypeptides, cell protectants etc) into a single cell. This setup can also be utilized to remove a composition from the cell, e.g. to remove a cell cryoprotectant.

To effect such transfer, a cell is first trapped between the electrodes (e.g. in the hole of the membrane) and the composition is injected into the upper chamber. Electrical pulses are generated between the electrodes in a closed electrical circuit, and the cell (trapped in the hole) acts as a switch for opening and closing the electrical circuit. When the applied electrical pulse is not sufficient to induce electroporation, for instance electrical fields of less than 100 V/cm, the cell acts as a closed switch. When the pulse is of sufficient magnitude for instance electrical fields in the range of 200 V/cm to 500 V/cm the cell membrane opens to ionic flow and electrical current flows through the circuit between the upper and lower chambers. This allows real time control over the opening and the closing of the cell membrane and enables controlled introduction of the composition into a single cell.

In a reverse process, the composition can be removed from the cell by the application of reversed electroporation and the presence of diluting buffer in the chambers.

Thus, the present cell preservation device can be used to introduce and remove compositions from single cells. For example, when cryopreservation of a single cell is desired, the cell can be micro-electroporated with cryoprotectant agent and then subjected to single cell directional solidification. To reverse the process, the present device will thaw the cryopreserved cells and the cryoprotectant agent will be removed by reverse micro-electroporation.

FIGS. 8-9 are fluorescent images of cells (ND1—prostate adenocarcinoma cells) stained with a fluorescent dye following single cell-electroporation in micro channels.

Example 3

Micro-Electroporation of Murine Mesenchymal Progenitors Using a Glass Micro-capillary Tube C3H10T1/2 cells stably transfected with the marker genes Green Fluorescent Protein (GFP) and Luciferase cells were suspended in DMEM high-glucose medium at a concentration of 1×105 cells/ml. Medium was supplemented with 75 uM Propidium Iodide (PI). The cell suspension was then injected through a glass micro-capillary (approximately 100 μm diameter at the narrow region) using syringe pump at a flow rate of approximately 50 μl/minute. Step square pulses of 0.5V for 100 ms, 9V for 100 ms and 0.5V for 100 ms, were generated through the capillary every 2 seconds using two electrodes flanking the cell trapping region. Individually electroporated cells were collected from the capillary and were observed under fluorescence microscope to determine the electroporation efficiency. Cells that have been electroporated demonstrated double labeling of GFP and PI, which has entered the cell due to membrane poration (FIG. 9).

Example 4

Mathematical Modeling of Magnetic Induction Sensing

This example illustrates how a cell tagged with magnetic or magnetizable particles can be distinguished from a non-tagged cell by measuring the phase shift between excitation and sensing coils.

Following the teachings of Griffiths et al. (Magnetic induction tomography—A measuring system for biological materials." Ann NY Acad Sci 873: 335-345, 1999), a biological specimen (e.g. cell) is considered as a simple circular disk of tissue of radius R and thickness t, placed centrally and midway between a small excitation coil and a small sensing coil spaced at a distance 2a. The thickness t, was considered to be much less than 2a. A sinusoidal current, of angular frequency ω, flows in the excitation coil and induces a magnetic field B. The circular disk has conductivity σ and relative permittivity $\epsilon_r$ (it is assumed that the skin depth is greater than, t, and therefore the attenuation produced by the disk is neglected).

This bulk model assumes that the effect of the magnetized (conductive) particles is uniformly distributed in the cell and that the occurrence of magnetized (conductive) particles will cause the bulk electrical parameters of the combined cell with particles to change relative to cells without particles according to the formula:

$$\sigma_c(T, F) = \frac{[(\sigma_t \cdot T) + (\sigma_f \cdot F)]}{100} \quad (1)$$

$$\varepsilon_{r,c}(T, F) = \frac{[(\varepsilon_{r,t} \cdot T) + (\varepsilon_{r,f} \cdot F)]}{100}$$

where the subscripts c, t, and f stand for the composite properties, the cell properties and conductive (magnetized) properties, respectively. The symbols, T, and, F, give the percentage volume of the pure tissue or the magnetized (conductive) particles respectively.

Phase Shift in the Sensing Coil

Considering the thin "tissue" disk model described above, a sinusoidal current of angular frequency ω, flows in the excitation coil and induces a magnetic field B in the sensing coil. According to Griffiths, the current induced in the "tissue" disk placed between the excitation and sensing coils causes a perturbation ΔB in the field of the sensing coil given by:

$$\frac{\Delta B}{B} = (\omega \varepsilon_o \varepsilon_r - j\sigma) \left( \frac{ta^3 \omega \mu_o}{2} \right) \left\{ \frac{1}{a^2} - \frac{a^2 + 2R^2}{(a^2 + R^2)^2} \right\} \quad (2)$$

where $\epsilon_0$ and $\mu_0$ are the permittivity and permeability of free space, respectively. The total magnetic field B+ΔB in the sensing coil is shifted relative to the primary magnetic field B by an angle θ. The magnetic field and its perturbation can be obtained from the voltages induced in the sensing coil, $V_i$ and $\Delta V_i$. ΔB/B can be defined in terms of the induced voltage in the sensing coil (Scharfetter et al. Biological tissue characterization by magnetic induction spectroscopy (MIS): requirements and limitations. IEEE Trans Biomed Eng 50(7): 870-80, 2003), by:

$$\frac{\Delta B}{B} = \frac{\Delta V_i}{V_i} \quad (3)$$

a constant k is defined:

$$k = \left( \frac{ta^3 \mu_o}{2} \right) \left\{ \frac{1}{a^2} - \frac{a^2 + 2R^2}{(a^2 + R^2)^2} \right\} \quad (4)$$

Substituting (3) and (4) into (2), the phase of the total induced voltage θ($V_{ind}$) in the sensing coil with respect to the induced voltage by the primary magnetic field could be expressed as a function of frequency and electrical parameters in the "tissue" disk between the coils, by:

$$\theta(V_{ind}) = \text{arc}tg\left(\frac{k\omega\sigma}{k\omega^2\varepsilon_0\varepsilon_r + 1}\right) \quad (5)$$

Phase Shift in the Excitation Coil

In cases where the magnetic field in the system is generated through an oscillator which supplies an excitation signal ($V_{exc}$) and through an output impedance, $Z_{out}$. The reference voltage ($V_{ref}$) measured in the excitation coil is given by expression (6) where $Z_L$ is the impedance of a coil composite made of the resistance $R_L$ and the inductance $X_L$, in series.

For instance, an excitation coil of radius r, of 2 cm, having five turns and being made from magnet wire AWG32 has an inductance (L) (calculated on the basis of Faraday's law) of approximately 40 µH. The $Z_L$ values in the frequency domain were estimated for $R_L=1\Omega$ and $X_L=\omega_L$. A typical output impedance of 50Ω was considered for the oscillator.

$$V_{ref} = V_{exc}\left(\frac{Z_L}{Z_{out} + Z_L}\right) \quad (6)$$

According to Hart L. et al (L. W. Hart, H. W. Ko, J. H. Meyer, D. P. Vasholz and R. I. Joseph. "A noninvasive electromagnetic conductivity sensor for biomedical applications." IEEE Trans Biomed Eng 35(12): 1011-1022, 1988, the presence of a conductive sample (the "tissue" disk between the coils) causes a change in the impedance of the excitation coil given by $\Delta Z_L = \Delta R_L + \Delta X_L$, where: $\Delta R_L$ is the increase in the coil resistance and $\Delta X_L$ is the increase in the coil inductance. The expressions for $\Delta R_L$ and $\Delta X_L$ were derived in Hart et al (above) as:

$$\Delta R = 32\pi^3 * 10^{-14} N^2 f^2 R'^3 I' \Delta \sigma \quad (7)$$

$$\Delta X = 64\pi^4 * 10^{-14} N^2 f^2 R'^3 I' \varepsilon_0 \Delta \varepsilon_r \quad (8)$$

where: $f=\omega/2\pi$ is the frequency of the excitation signal, N is the number of coil turns, R' is the coil radius, $\varepsilon_0$ is the permittivity of free space, and $\varepsilon_r$ and σ are the relative permittivity and electrical conductivity of the "tissue" disk sample respectively. The term I' is a positive definite constant determined for a specific geometry. In this example substitutions of $\sigma_c \rightarrow \Delta\sigma$ and $\varepsilon_{r,c} \rightarrow \Delta\varepsilon_r$ were made for the expressions (7) and (8) because changes in electrical conductivity and relative permittivity of the "tissue" sample are also considered. The phase of the reference voltage $\theta(V_{ref})$ with respect to the excitation signal in the presence of a "tissue" sample can be estimated from the following expression:

$$\theta(V_{ref}) = \text{arc}tg\left[\text{Im}\left[\frac{Z_L + \Delta Z_L}{Z_{out} + Z_L + \Delta Z_L}\right] \bigg/ \text{Re}\left[\frac{Z_L + \Delta Z_L}{Z_{out} + Z_L + \Delta Z_L}\right]\right] \quad (9)$$

The total change in phase shift (Δθ) between the reference and induced voltages in the excitation and sensing coil respectively is given by the expression:

$$\Delta\theta = \theta(V_{ind}) - \theta(V_{ref}) \quad (10)$$

The changes in this value can be used to compare a tagged cell to a non-tagged cell.

Example 5

Mathematical Modeling of Cell Flow Control

This is an example of an extreme condition in which the flow of cell tagged with magnetic particles is halted by the application of an electromagnetic field. The flow of the cell inside a capillary tube is stopped using an external magnetic field. In general, a magnetic dipole will experience a force in a changing magnetic field. The force is proportional to the magnetic field gradient so if B is the magnetic field and u is the magnetic dipole moment $$F = \mu \frac{dB}{dx} N$$

where N is the number of beads on the cell.

In order to stop the cell, the force should be equal to the force that is driving the cell through the capillary which is simply F=ma where m is the cell's mass and a is its acceleration. So in order to stop the cell one needs to create a magnetic field which is a linear function of x (which is the direction of the capillary):

$$B = \frac{ma}{\mu N} x$$

The magnetic field needed can be calculated using the following parameters:
1. Cell mass m=1 nanogram $10^{-12}$ kilogram
2. Cell acceleration in the capillary $a=10^{-3}$ meter/sec$^2$
3. Dipole moment is the pole strength times the bead's diameter $\mu=10^{-9} \cdot 10^{-6} = 10^{-15}$ Ampere meter$^2$
4. Number of beads per cell N=1000

These rough estimates give a field gradient of $10^{-3}$ Teslas per meter inside the capillary which is very small and thus can be easily achieved using laboratory equipment.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for qualifying and manipulating cells of a cell sample labeled with a magnetic or magnetizable moiety comprising:
   (a) a cell sample holder for holding a cell of said cells; and
   (b) a first cell analyzer including:
      (i) a magnetic field source for applying a magnetic field to said cell; and
      (ii) a sensor for qualifying and/or quantifying an effect of said magnetic field on said cell; and (c) an electroporation chamber, wherein said cell sample holder is a capillary tube and said magnetic field source and said sensor are each separately arranged around the circumference of said capillary tube.

2. The system of claim 1, further comprising a second cell analyzer for qualifying and/or quantifying a feature of said cell.

3. The system of claim 2, wherein said second cell analyzer is capable of detecting a morphological feature of said cell, a biochemical feature of said cell, a molecular feature of said cell, an electrical feature of said cell, a flow dynamics feature of said cell, a density of said cell, a membrane permeability feature of said cell or an optical feature of said cell.

4. The system of claim 1, wherein said electroporation chamber is capable of facilitating the introduction or removal of molecules from the cells or/and facilitating preservation of said cell or is capable of destroying said cell.

5. The system of claim 1, wherein said magnetic field is an electromagnetic field.

6. The system of claim 1, wherein said magnetic field source and said sensor are electromagnetic coils.

7. The system of claim 1, wherein said first cell analyzer is capable of producing a transient magnetic field.

8. The system of claim 1, wherein an internal diameter of said capillary tube is selected so as to restrict passage therethrough to a single cell.

9. The system of claim 1, wherein said magnetic field source is capable of generating a pulsating magnetic field.

10. The system of claim 1, wherein said magnetic field source is capable of generating a magnetic field of alternating polarity.

11. The system of claim 10, wherein said magnetic field source is capable of varying a polarity shift of said magnetic field of alternating polarity.

12. The system of claim 1, further comprising a cell manipulator capable of manipulating said cell based on said effect of said magnetic field on said cell.

13. The system of claim 1, further comprising a cryopreserver.

14. A method of identifying cells of interest in a cell sample with the system of claim 1 comprising:
 (a) labeling the cells of interest with at least one type of a magnetic or magnetizable moiety;
 (b) exposing each cell of the cell sample in said cell sample holder to a magnetic field from said magnetic field source;
 (c) measuring a response of each cell of the cell sample to said magnetic field with said sensor; and
 (d) identifying the cells of interest according to said response.

15. The method of claim 14, wherein said response is current generated in a coil by a magnetic field of said magnetizable moiety.

16. The method of claim 14, further comprising the step of analyzing at least one feature of at least a subset of cells of the cell sample prior to, during or following step (b).

17. The method of claim 16, wherein said at least one feature is selected from the group consisting of a morphological feature, a biochemical feature, a molecular feature, an electrical feature, a flow dynamics feature, a density feature, a membrane permeability feature or an optical feature.

18. The method of claim 14, further comprising the step of manipulating cells of interest.

19. The method of claim 14, further comprising the step of separating said cells of interest from the cell sample according to said response.

20. The method of claim 18, wherein said manipulating includes subjecting the cells of interest to an electroporation field.

21. The method of claim 14, further comprising the step of cryopreserving the cells of interest.

22. The method of claim 14, wherein said subset of cells includes unlabeled cells.

23. The method of claim 14, wherein said subset of cells includes the cells of interest.

24. The method of claim 14, wherein said cells of interest are labeled with two types of magnetic or magnetizable moieties and whereas step (d) includes identifying of cells labeled with one type of said two types of magnetic or magnetizable moieties or with said two types of magnetic or magnetizable moieties.

25. The method of claim 14, wherein step (d) is effected by measuring an effect of a magnetic field generated by said at least one magnetic or magnetizable moiety on an induction coil.

26. The method of claim 14, wherein said magnetic field is a pulsating magnetic field source.

27. The method of claim 14, wherein said magnetic field is of alternating polarity.

28. The method of claim 27, wherein said magnetic field of alternating polarity is of varying polarity shift.

29. The method of claim 14, wherein the cell sample is a biological sample.

30. The method of claim 14, wherein the cells of interest are stem cells.

31. The method of claim 30, wherein said stem cells are adult stem cells.

32. The method of claim 31, wherein said adult stem cells are hematopoietic stem cells.

33. The method of claim 31, wherein said adult stem cells are mesenchymal stem cells.

34. The method of claim 14, wherein the cells of interest are fetal cells.

* * * * *